United States Patent [19]
Buelow et al.

[11] Patent Number: 5,756,492
[45] Date of Patent: May 26, 1998

[54] GRAFT SURVIVAL PROLONGATION WITH PORPHYRINS

[75] Inventors: Roland Buelow, Palo Alto; Jacky Woo, Sunnyvale; Suhasini Iyer, San Ramon, all of Calif.

[73] Assignee: SangStat Medical Corporation, Menlo Park, Calif.

[21] Appl. No.: 709,650

[22] Filed: Sep. 9, 1996

[51] Int. Cl.$^6$ .......................... A61K 31/33; A61K 31/555
[52] U.S. Cl. ............................................. 514/185; 514/183
[58] Field of Search ..................................... 514/183, 185

[56] References Cited

U.S. PATENT DOCUMENTS

| | | | |
|---|---|---|---|
| 4,829,984 | 5/1989 | Gordon | 600/12 |
| 5,563,132 | 10/1996 | Bodaness | 514/185 |

OTHER PUBLICATIONS

Abraham, N.G., et al., "The Physiological Significance of Heme Oxygenase," *Int. J. Biochem.*, 20(6):543–558 (1988).

Vulapalli, S.R. and M.D. Maines, "Coordinated Expression and Mechanism of Induction of HSP32 (heme oxygenase–1) mRNA by Hyperthermia in Rat Organs," *Biochimica et Biophysica Acta*, 1217:273–280 (1994).

Neil, T.K., et al., "Modulation of Corneal Heme Oxygenase Expression by Oxidative Stress Agents," *Journal of Ocular Pharmacology and Therapeutics*, 11(3):455–468 (1995).

Haga, Y., et al., "Unconjugated Bilirubin Inhibits in vitro Major Histocompatibility Complex–Unrestricted Cytotoxicity of Human Lymphocytes," *Biochimica et Biophysica Acta*, 1316:29–34 (1996).

Willis, D., et al., "Heme Oxygenase: A Novel Target for the Modulation of the Inflammatory Response," *Nature Medicine*, 2(1):87–90 (1996).

Agarwal, A., et al., "Gas–Generating Systems in Acute Renal Allograft Rejection in the Rat," *Transplantation*, 61:93–98 (1996).

Maines, M.D., "Zinc–Protoporphyrin in a Selective Inhibitor of Heme Oxygenase Activity in the Neonatal Rat," 673:339–350 (1981).

Drummond, G.S. and A. Kappas, "Preventioin of Neonatal Hyperbilirubinemia by Tin Protoporphyrin IX, a Potent Competitive Inhibitor of Heme Oxidation," *Proc. Natl. Acad. Sci. USA*, 78(10):6466–6470 (1981).

Tenhunen, R., et al., "Microsomal Heme Oxygenase: Characterization of the Enzyme," *The Journal of Biological Chemistry*, 244(23):6388–6394 (1969).

*Primary Examiner*—Kimberly Jordan
*Attorney, Agent, or Firm*—Richard F. Trecartin

[57] ABSTRACT

Metalloporphyrins are administered in conjunction with transplantation to enhance the survival of the organ.

13 Claims, 1 Drawing Sheet

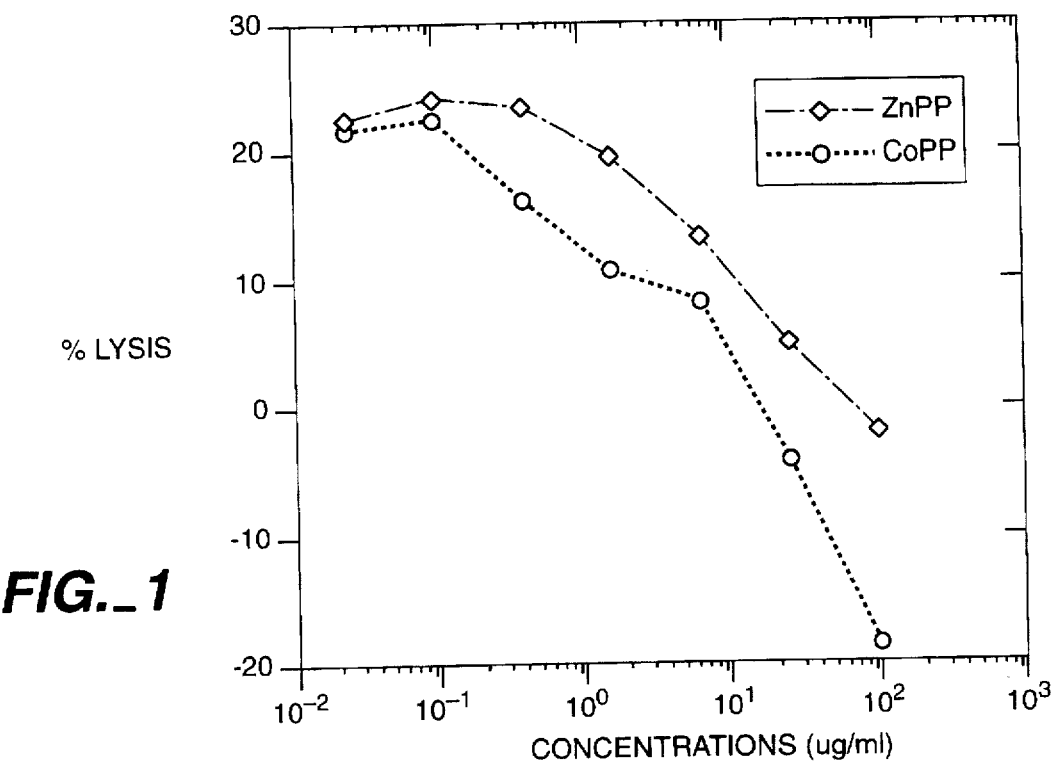
FIG._1
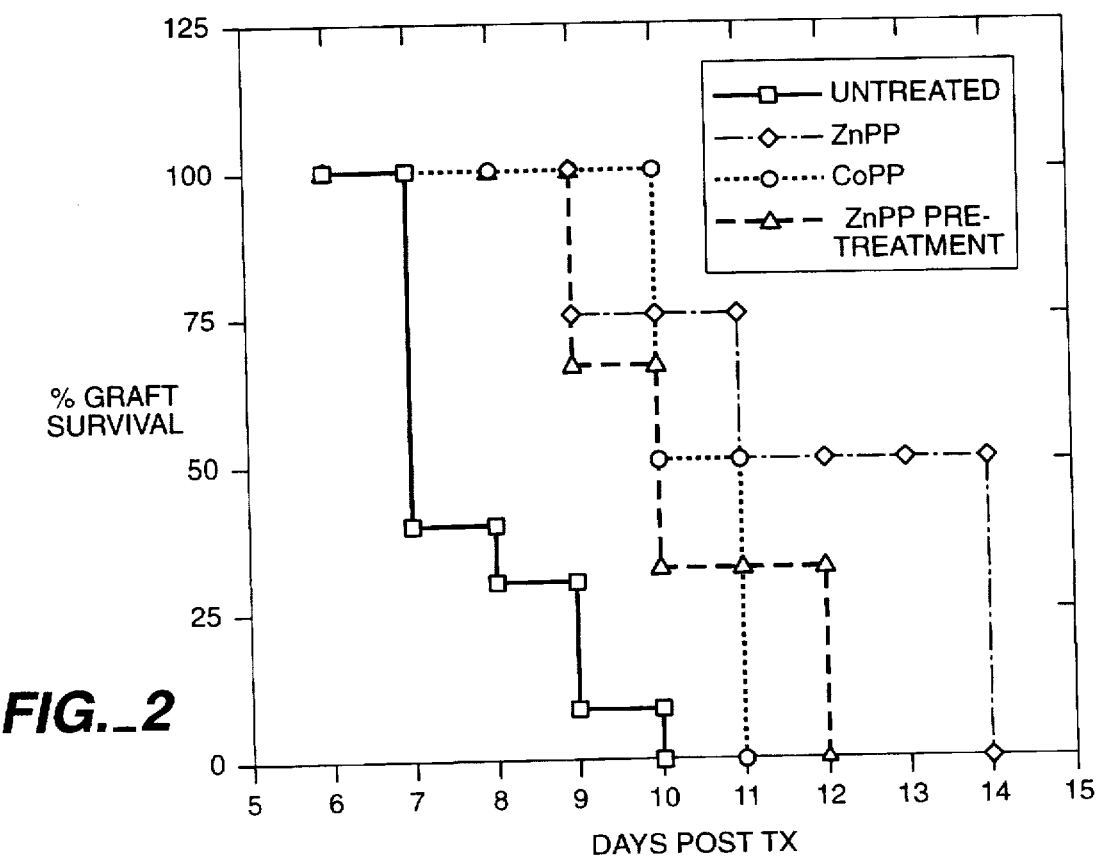
FIG._2

GRAFT SURVIVAL PROLONGATION WITH PORPHYRINS

BACKGROUND

The inflammatory process is an extraordinarily complex process, varying with the cause of inflammation, the site of the inflammation, and the nature of the insult. Numerous different types of leukocytes are attracted to the site where the inflammatory process is initiated. The different leukocytes initiate different biological processes to respond to the insult. While in many situations, the inflammatory response is healthy in destroying a pathogen, in other situations, such as autoimmune diseases and transplantation, the inflammatory response is undesirable. In the latter case, this leads to rejection and loss of the implanted organ, which in most cases will be fatal.

A number of different avenues have been investigated to encourage the retention of allografts. For the most part, these avenues have involved general immunosuppression, using drugs such as cyclosporin and FK 506. Extensive efforts have been directed to inducing anergy toward the foreign tissue. Also, the role of various factors has been investigated, where by modulating the level of the factors, the immune response may be diminished. For the most part, the primary approach has been the use of drugs which suppress the entire immune system, therefore leaving the patient vulnerable to adventitious infection.

Because of the restricted availability of donor organs, consideration has been given to using xenografts for temporary maintenance, while an acceptable allogenic organ is identified. The xenografts not only differ as to the MHC, but will also have numerous other epitopes differing from the host. Therefore, additional rejection mechanisms are brought to bear against the xenograft.

There is a pressing need to find alternative modalities which provide protection against transplant rejection. These modalities may find use in conjunction with other drugs, where lower levels of other drugs having significant side effects may be used effectively, so as to reduce the detrimental side effects. Thus, there is substantial interest in developing new approaches to reducing the rejection phenomenon, where the drug may act by itself or in conjunction with other drugs.

BRIEF DESCRIPTION OF THE RELEVANT LITERATURE

Heme oxygenase has been the subject of numerous studies as evidenced by the review article, Abraham et al., *Int. J. Biochem.* (1988) 20(6):543–558. Recently, modulation of heme oxygenase activity has been described in Raju and Maines, *Biochimica et Biophysica Acta* (1994) 1217:273–280; Neil et al. *J. of Ocular Pharmacology and Therapeutics* (1995) 11(3):455–468; Haga et al., ibid. (1996) 1316:29–34; Willis et al., *Nature Medicine* (1996) 2(1):87–90; and Agarwal et al., *Transplantation* (1996) 61(1):93–98.

SUMMARY OF THE INVENTION

Transplant survival in mammalian hosts is enhanced by providing a therapeutic dose of a metallic protoporphyrin in conjunction with the transplantation. Specifically, inhibitory metallic protoporphyrins are employed in an amount sufficient to inhibit heme oxygenase at a time proximal to the time of transplant, whereby the survival of the transplant is extended.

BRIEF DESCRIPTION OF THE DRAWINGS

FIG. 1 is a graph of the inhibition of target cell lysis by metalloprotoporphyrins. T-cell mediated cell lysis was evaluated in the presence of varying amounts of Zn- and Co-protoporphyrin in a four hour chromium release assay;

FIG. 2 is a graph showing the prolongation of heart allograft survival following metalloprotoporphyrin therapy. CBA recipients of C57B1/6 heart allografts were either untreated or treated as follows: ZnPP group (n=4); Zn-protoporphyrin was administered at 10 mg/kg/day on day −1 before transplantation and on days 1–9 post transplantation. CoPP group (n=4); Co-protoporphyrin was administered at 20 mg/kg/day on days 0–5 post-transplantation; ZnPP pretreatment group (n=3); heart donors were treated one day before transplantation with 50 mg/kg Zn-protoporphyrin.

DESCRIPTION OF THE SPECIFIC EMBODIMENTS

Methods are provided for prolonging the acceptance of transplants in a mammalian host. The method employs the administration of a metalloprotoporphyrin prior to concomitant with, subsequent to or a combination thereof with the transplant. A particular regimen is employed for administration, where a single bolus or plurality of doses may be administered to the recipient and/or donor, before, concomitant with, or subsequent to the implanting of the organ in the recipient. The particular protocol will depend upon the nature of the organ, the particular metalloprotoporphyrin which is employed, and the use of other immunosuppressants.

Adminstration will usually begin within 7 days prior to the transplant, preferably within about 3 days, and desirably will include the day prior to the transplant and particularly, the same day as and/or the day after the transplantion. Administration may be on consecutive days or non-consecutive days, generally any gap being fewer than 10 days. Adminstration concomitant with the transplant or on the same day may be useful, but preferably in most instances administration will begin on the first day after the transplant and may be continued until the transplant is stabilized, generally not exceeding one month, more usually not exceeding two weeks. The metalloprotoporphyrin may also be administered to the donor, usually within three days of the removal of the organ, more usually not later than the day prior to removal of the organ, desirably within about 12 hours of the removal of the organ.

A number of different metalloprotoporphyrins are known, which have been used for the inhibition of heme oxygenase. Depending upon the nature of the particular metal which is chelated by the protoporphyrin, and the protocol employed, either induction or inhibition of the heme oxygenase is observed. Contradictory reports exist in the literature as to the effect of the particular metal. Abraham et al., *Int. J. Biochem.* (1988) 20(6):543–558 report that tin, cobalt, zinc and manganese act as competitive inhibitors of the enzyme, while Neil et al., *J. of Ocular Pharmacology and Therapeutics* (1995) 11(3):455–468, and Maines, *Biochim. et Biophys. Acta* (1981) 673:339–350 concur that zinc and tin inhibit, but indicate that cobalt induces activity. Therefore, the role of the metalloporphyrins in the prolongation of the survival of the graft will be associated with the modulation of heme oxygenase I activity.

The metalloprotoporphyrins of interest in this invention include iron, cobalt, tin, zinc, and manganese, particularly cobalt and zinc.

The subject compounds may be formulated in a variety of ways, depending upon the nature of administration, the particular metalloprotoporphyrin, the number of administrations, other drugs, and the like. Therefore, the administration may vary with whether the donor, recipient or organ is being treated, the number of administrations, the manner of administration, the presence of other active components, and the like. The formulation will generally be in a physiologically acceptable form, using various carriers, such as water, deionized water, phosphate buffered saline, aqueous ethanol, vegetable oils, etc. In some instances, the formulation may be formulated as a slow release formulation, where the subject compounds may be encapsulated in a wide variety of carriers, may be administered as capsules, or as a prodrug. The subject compounds may be taken parenterally or orally, generally being administered intravascularly, subcutaneously, or intramuscularly. Depending upon the manner of administration, and the frequency of administration, the dosage will generally be in the range of about 0.5 to 50 mg/kg.

When bathing the organ in a composition comprising the subject compound, conventional medium may be used, such as organ preservation solution. The temperature at which the organ may be maintained will be conventional, generally in the range of about 1° C. to 8° C. The residence time of the organ in the medium will generally be in the range of about 2 to 48 h, more usually 2 to 24 h.

When administered parenterally, generally the total amount of the subject compound per day will generally be in the range of about 0.5 to 50, more usually in the range of about 1 to 25 mg/kg/day. This dose may be in a single bolus or be divided up to be administered in portions to provide the desired level of the subject compound in the host.

The subject compositions may be used with a wide variety of hosts, particularly primates, more particularly humans, or with domestic animals, and the like. The subject compositions may be used in conjunction with the transplantation of a wide variety of organs, such as kidney, heart, liver, spleen, bone marrow, pancreas, lung, islet of langerhans, etc.

The subject compositions may be used as adjunctive therapy with immunosuppresssant compounds, such as cyclosporine, FK506, MHC Class I oligopeptides, or other immunosuppressants, where reduced amounts of the immunosuppressant may be used, generally reducing the amount employed by at least 25%, more usually at least 40% or more, from the therapeutic dosage for the indication.

Generally, the graft life will be extended for at least three days beyond what could normally be anticipated in the absence of the subject compound, more usually at least five days. This can be useful in areas where xenogeneic grafts have been used awaiting an allogenic graft, to allow for reduced amounts of immunosuppressants or avoid using immunosuppressants altogether.

The subject compounds may be used for allogenic, as well as xenogenic, grafts.

EXPERIMENTAL

The following examples are offered by illustration and not by way of limitation.

Materials and Methods

Animals: Male, 7–8 week old CBA/J (H-$2^k$) and C57BL/6/J (H-$2^b$) mice were purchased from the Jackson Laboratory (Bar Harbor, Me.). Mice were maintained in our animal facility following Animal Welfare Guideline, Department of Health, CA.

Synthetic Metalloporphyrins: Various synthetic metalloporphyrins were purchased from Porphyrin Products, Inc. (Logan, Utah). They were dissolved in 0.2M NaOH, adjusted to pH 74, with 1M HCl and subsequently diluted to 1 mg/ml in PBS.

Cytotoxic T-cell Activity: To assay the effect of metalloprotoporphyrins on cytotoxic T-cell activity, CBA to B6 effectors were generated following a five day culture of $3 \times 10^6$ CBA spleen cells with $3 \times 10^6$ mitomycin-treated B6 spleen cells in wells of a 24-well plate (Nunclone Delta, Nunc, Denmark) in R-10 medium. Effector cells were then harvested and washed. (H2b), a mouse lymphoma induced in C57BL/6N was used as target cells. EL4 cells were routinely subcultured once every three days. They were then collected, washed, and labeled with 0.1 mCi of sodium chromate-51 in 200 μl for one hour at 37° C. Effector (E) and target (t) cells were added into V-shaped tissue culture plates (Nunc, Denmark) at E:T of 20:1. Metalloprotoporphyrins were diluted to the working concentrations with PBS and added at the beginning of the four hour incubation period. For the determination of maximal release, 1% triton X-100 was added to separate wells. Plates were centrifuged for three minutes to increase cellular contact before the four hour incubation period. After incubation 75 μl supernatant from each well was collected and the amount of $^{51}Cr$ released was counted using a TopCount scintillation counter. The degree of cell lysis was calculated using the formula below:

$$\% \text{ lysis} = \frac{CPM_{experimental} - CPM_{spontaneous}}{CPM_{total} - CPM_{spontaneous}} \times 100$$

Heterotopic Heart Transplantation: Abdominal heterotopic heart transplantation was performed as previously described by Ono and Lindsey (J. thorac. Cardiovasc. Surg. 1969 7:225–229) using C56B1/6 donors and CBA recipients. Metalloporphyrin was administered intraperitoneally using various protocols. Heart allograft survival was monitored daily by direct palption, and rejection was defined as termination of palpable cardiac contractility. Results are expressed as percentage graft survival at a given postoperative period. Statistical analysis was performed with the Mann-Whitney test.

Results

Zinc- and cobalt-protoporphyrin inhibit cytotoxicity in vitro. The effect of Zn- and Co-protoporphyrins on T- and NK-cell mediated cytotoxicity was evaluated in an in vitro four hour chromium release assay. Results of a representative experiment using cytotoxic T-cells are shown in FIG. 1. Similar results were observed in NK-cell assays. Addition, of protoporphyrin to the tissue culture inhibited target cell lysis in a dose dependent manner. At about 10 μg/ml target cell lysis was inhibited completely (0% lysis). At even higher concentrations, chromium release from target cells in the presence of protoporphyrins was lower than the spontaneous release observed in the absence of the compounds. These results demonstrate modulation of HO activity by metalloporphyrins results in inhibition of cytotoxicity in vitro.

Zinc- and cobalt-protoporphyrin therapy of heart allograft recipients results in prolongation of graft survival. The effect of metalloprotoporphyrins therapy on heart allograft survival was evaluated in a mouse model. CBA recipients of C57B1/6 hearts were treated following transplantation with several doses of Zn- or co-protoporphyrin. Compared to control animals (mean survival time=7.8±1.1) heart allograft survival was significantly prolonged to 12.0±2.4 (p=0.008) and 10.5±0.6 (p=0.004) days in Zn- or Co-protoporphyrin treated animals, respectively. Pre-treatment of heart donors one day before transplantation resulted in a prolongation of graft survival to 10.3±1.5 days (p=0.03).

It is evident from the above results, that by using metalloprotoporphyrins, one can greatly extend the survival of implants in a host. The compounds have few side effects and can be used safely with positive results.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for extending the survival of an organ transplant in a recipient, said method comprising:
    contacting said organ transplant with a metalloprotoporphyrin in an amount sufficient to extend the survival time of said transplant.

2. A method according to claim 1, wherein said contacting is ex vivo.

3. A method according to claim 1, wherein the step of contacting comprises contacting said organ transplant with said metalloprotoporphyrin on day one subsequent to the transplantation of said organ in said recipient.

4. A method according to claim 3, wherein the step of contacting comprises contacting said organ transplant with multiple dosages of said metalloprotoporphyrin within a period of two weeks.

5. A method according to claim 3 further comprising administering said metalloprotoporphyrin prior to transplant of said organ.

6. A method according to claim 1, wherein the step of contacting comprises administering said metalloprotoporphyrin to the donor of said organ prior to removal of said organ from said donor.

7. A method for extending the survival of an organ transplant in a recipient, said method comprising:
    administering parenterally to the recipient of said organ transplant at least one of a cobalt or zinc metalloprotoporphyrin in an amount sufficient to extend the survival time of said transplant, said step of administering comprising administering to said recipient said at least one of said cobalt or zinc metalloprotoporphyrin at least on day one after the transplant.

8. A method according to claim 7, wherein the step of administering comprises administering to said recipient repeated dosages during a period of two weeks after said transplant.

9. A method according to claim 8, wherein said transplant is an allograft.

10. A method according to claim 9, wherein said allograft is a heart.

11. A method according to claim 8, wherein said metalloprotoporphyrin is zinc metalloprotoporphyrin.

12. A method according to claim 8, wherein said metalloprotoporphyrin is cobalt metalloprotoporphyrin.

13. A method for extending the survival of an organ transplant in a recipient, said method comprising:
    contacting said organ transplant with a compound capable of modulating heme oxygenase I activity in an amount sufficient to extend the survival time of said transplant.

\* \* \* \* \*